United States Patent [19]

Bukowiecki et al.

[11] 4,446,718

[45] May 8, 1984

[54] METHOD AND APPARATUS FOR REDUCING FALSE ALARMS IN GAS WARNING INSTALLATIONS CAUSED BY SPURIOUS GASES

[75] Inventors: Stanislaw Bukowiecki, Uerikon; Karlheinz Paglotke, Langnau a. Albis, both of Switzerland

[73] Assignee: Cerberus AG, Männedorf, Switzerland

[21] Appl. No.: 415,038

[22] Filed: Sep. 7, 1982

[30] Foreign Application Priority Data

Sep. 22, 1981 [CH] Switzerland .......................... 6115/81

[51] Int. Cl.³ .............................................. G01N 27/14
[52] U.S. Cl. .......................................... 73/23; 340/634
[58] Field of Search ................. 73/23, 27 R; 324/71.5; 340/634; 422/98

[56] References Cited

U.S. PATENT DOCUMENTS 3,906,473  9/1975  Le Vine ............................... 340/634
4,012,692  3/1977  Eicker .................................... 422/98
4,185,491  1/1980  Owen ................................... 73/27 R

FOREIGN PATENT DOCUMENTS 1474080  5/1977  United Kingdom .
1526751  9/1978  United Kingdom .

*Primary Examiner*—Stephen A. Kreitman
*Attorney, Agent, or Firm*—Werner W. Kleeman

[57] ABSTRACT

A metal-oxide semiconductor, which is heated to different temperatures, is used in conjunction with an electronic circuit for reducing false alarms caused by spurious gases in gas warning installations and for determining the composition of a gas mixture. The temperature of the metal-oxide semiconductor, after reaching a predetermined value (T), is altered by an amount ($\Delta T$) either towards the positive or negative side or towards both the positive and negative side, respectively. The thus caused change in the conductivity of the metal-oxide semiconductor is evaluated in a comparator and in circuits for the different peak values of the gas components.

7 Claims, 4 Drawing Figures

METHOD AND APPARATUS FOR REDUCING FALSE ALARMS IN GAS WARNING INSTALLATIONS CAUSED BY SPURIOUS GASES

BACKGROUND OF THE INVENTION

The present invention relates to a new and improved method of, and apparatus for, reducing false alarms in gas warning installations which are caused by spurious gases, and furthermore, serves for determining the composition of a gas mixture, wherein there is used a metal-oxide semiconductor as the gas-sensitive element, this semiconductor being heated to a substantially constant temperature.

It is of utmost importance to provide warning and protection against toxic and explosive gases or chemical vapors, as the case may be, and such warning and protection-installations are presently used in the chemical industry, in traffic facilities, such as garages and tunnels, and in heating installations. There are already available in the market metal-oxide semiconductors which can be used as sensors for this purpose. The semiconductors, when in a heated state, react to reducing gases and vapors as well as $H_2O$ located in their surroundings by changing their conductivity. This change in conductivity for the semiconductors is beneficially utilized as an indicator of the presence of integral gas concentrations. However, the sensors do not give any information as to which gas components or which chemical vapors they have encountered. Those skilled in the art classify this phenomenon by designating such sensors or detectors as "sensors" which have a "wide-band" response behavior as concerns the gas sensitivity. In contrast thereto, there exists the requirement of determining the course of the concentration of an individual gas or vapor component. This requirement which is present in practical applications has been fulfilled in that, there have been fabricated special gas sensors for a certain gas, for instance selective $H_2S$ sensors, or for a certain vapor, or that a metal-oxide semiconductor is designed to contain forwardly arranged filters which block undesired gases. What is here disadvantageous is that by providing such an absolute selectivity it is not possible to reliably detect other dangerous gas components or vapor components which simultaneously are located in the surroundings. This will be more fully explained in conjunction with two examples. In a garage there is installed a gas warning installation which selectively responds to carbon monoxide (CO). Gasoline vapors which are formed, for instance, by accidental spilling of gasoline, are therefore not detected. In order to also be able to detect this dangerous gas it is necessary to use wide-band metal-oxide semiconductors which are responsive both to CO and also to the gasoline vapors. By virtue of this compromise there is, however, again reintroduced the problem of false alarms as will be easily discernible from the following considerations. The metal-oxide semiconductor responds with similar sensitivity to both CO and gasoline vapors. Yet, the concentration of noxious carbon monoxide, at which there must be initiated protective measures to protect human beings, amounts to around approximately 50 ppm, whereas gasoline vapors first tend to become explosive at much higher concentrations. The metal-oxide semiconductor, for instance if set to a sensitivity for the detection 50 ppm CO, therefore will erroneously simulate an alarm situation even if there is present a harmless concentration of gasoline vapors. It is for this reason that previously one intentionally dispensed with the detection of the gasoline vapors, so that there were not initiated defensive or protective measures which are especially designed for this purpose.

As the second example mention is made of subterranean communication facilities which are usually run by postal authorities, at least in many European countries, and which are endangered by explosions due to the diffuse intrusion of gases from the public gas pipeline network. Additionally, there are provided in the rooms or areas containing the communication installations accumulators serving for furnishing an emergency current supply and which during their operating times produce hydrogen ($H_2$). Therefore, to initiate suitable and specific protective measures there exists in such rooms the necessity of being able to distinguish between $H_2$ as a spurious gas and the explosion-prone gases originating from the gas supply network. Also in this case hydrogen triggers false alarms which heretofore were intentionally tolerated, that is to say, the air circulation and venting installations frequently were unjustifiably turned-on and there was wasted a great deal of electrical energy.

In German Patent Publication No. 2,313,413 and the corresponding U.S. Pat. No. 4,012,692, granted Mar. 15, 1977 there is disclosed a method for the determination of the content of gas components in a gas mixture by means of metal-oxide semiconductors. The metal-oxide semiconductor is specially set to the CO-components in a gas mixture which are encountered in mines. This metal-oxide semiconductor is heated to an upper temperature by a heating wire. During and after the uncontrolled cooling phase down to room or ambient temperature there is accomplished the CO-measurement which is differentiated and integrated at a subsequently connected electronic evaluation circuit. This evaluation only is accomplished at the moment where there is not undertaken any measurement. What is disadvantageous with this prior art equipment is that the described apparatus is only responsive to one gas component and the evaluation operation is separated in time from the measuring operation. The last-mentioned mode of operation leads to delays in giving an alarm.

In order to explain the previous comments somewhat better as concerns the metal-oxide semiconductors reference will be made shortly in this disclosure to FIG. 1 which illustrates the known response behavior of such semiconductor with response profiles, for instance, for two gases.

SUMMARY OF THE INVENTION

Therefore, with the foregoing in mind it is a primary object of the present invention to provide a new and improved method and apparatus for reducing false alarms caused by spurious gases in gas warning installations and/or for reliably determining the composition of a gas mixture.

Another and more specific object of the present invention is directed to completely utilizing the wide-band sensitivity of metal-oxide semiconductors and in the presence of gas or vapor components, which could lead to giving an alarm, additionally, also determining the nature of the gas or vapor component.

Yet a further significant object of the present invention is to provide an alarm device as part of a gas warning system, which is individually programmable to a predetermined gas and vapor pair.

Still a further significant object of the invention is directed to a method and apparatus for reliably reducing false alarms caused by spurious gases in gas warning installations, wherein there can be initiated the defensive measures which are specific for each gas and vapor component.

A further significant object of the present invention is directed to a new and improved method and apparatus for reducing false alarms caused by spurious gases in gas warning installations, wherein the entire installation is constructed and designed to contain simple means possesses low fabrication costs, and additionally, there is afforded simple maintenance and servicing of the installation during the operating times.

It is yet a further object of the invention to ensure for the compatibility of the programmable alarm devices with already existing gas warning installations.

Now in order to implement these and still further objects of the invention, which will become more readily apparent as the description proceeds, the inventive method for reducing false alarms in gas warning installations which are caused by spurious gases, and wherein there is used as the gas-sensitive element a metal-oxide semiconductor which is operated at an essentially constant temperature, is manifested by the features that in the presence of an output signal caused by an unknown gas or vapor composition, and which output signal is predicated upon a change in conductivity of the gas-sensitive element, there is rapidly altered its temperature, and the sign as well as the magnitude of the thus caused additional change in the output signal is inputted to an electronic circuit for discriminating the spurious gas.

According to a further method aspect of the invention for the determination of the composition of a gas mixture by means of a gas-sensitive element which is constructed as a metal-oxide semiconductor, and which is heated to an essentially constant temperature, it is contemplated that in the presence of an output signal of the gas-sensitive element its temperature is rapidly altered towards the positive or negative side, and the thus caused signal change is superimposed in accordance with its magnitude and sign upon the output signal and inputted to an electronic circuit.

As alluded to above, the invention is not only concerned with the aforementioned method aspects, but also relates to a new and improved construction of apparatus for the performance thereof. According to an exemplary embodiment of the inventive apparatus there is provided a comparator which receives the output signal of the gas-sensitive element constructed as a metal-oxide semiconductor. This comparator switches-on a switching circuit for a first peak value. Additionally, there is provided an analog value-comparator which accomplishes programmable changes in the temperature of the semiconductor for discriminating the spurious gas.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
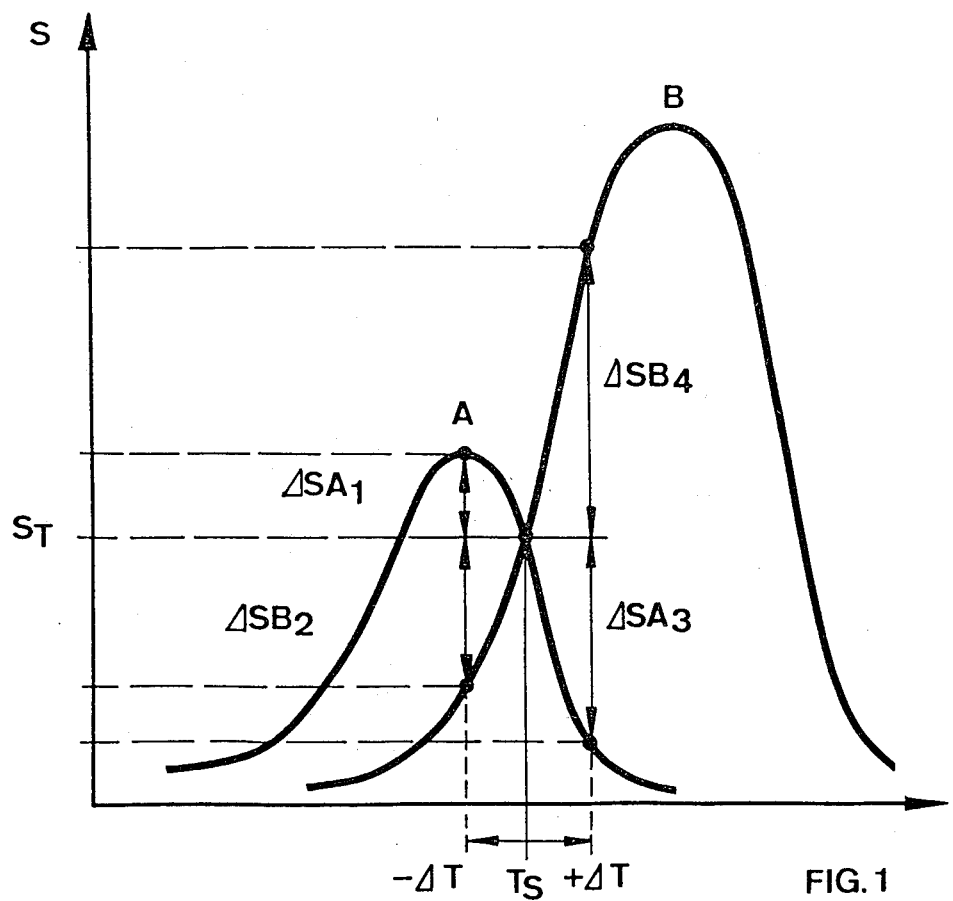
FIG. 1 is a diagram depicting the response behavior of a gas or vapor-sensitive metal-oxide semiconductor.

Describing now the drawings, in FIG. 1 there has been plotted along the abscissa the temperature to which there is heated the metal-oxide semiconductor. Along the ordinate there is plotted the changes in conductivity of the semiconductor at the different heating temperatures. As an example there have only been illustrated the so-called response profiles of two different gases or vapors A and B. It is particularly mentioned that the conductivity of the semiconductor is markedly different at different temperatures in the surroundings of gases; this means that gases or vapors having the same concentration produce output signals having different voltage or potential values. That is the reason why heretofore it was not possible to carry out an exact evaluation of the nature of the gas or the nature of the vapor.

In FIG. 1 both of the gases A and B are representative for a gas pair. The previously discussed first example involving a garage can be related to such FIG. 1. In this case the gas A would be carbon monoxide (CO) and the spurious gas B the gasoline vapors. By means of the invention, which will be described more fully hereinafter in conjunction with FIGS. 2 and 3, it is intended to achieve the result that the gas alarm is only automatically initiated in the presence of the component A, i.e., the carbon monoxide. The metal-oxide semiconductor is set to the temperature $T_S$ which can amount to, for instance, approximately 300° C. This setting is accomplished by an electrical heater. Now if carbon monoxide (component A) or gasoline vapors (component B) are present in the neighborhood of the semiconductor then there is formed a conductivity $S_T$ of the semiconductor. This is inputted to the electronic circuit depicted in FIG. 3 and evaluated by such circuitry in a manner such that there is produced a so-called pre-warning or incipient warning. In this case, the electrical heating of the semiconductor is controlled by the electronic circuitry such that the temperature T is lowered by the amount $-\Delta T$. For the desired target component A which is to be detected there results an increase in the output signal of the semiconductor by the amount $\Delta SA_1$. For the spurious component B there results a reduction in the output signal by the amount $\Delta SB_2$. Consequently, there is exactly prescribed for the electronic circuit the discrimination between both of the components A and B, so that it can initiate the protective or defensive measures needed for the elimination of the target component A. This desired function is accomplished notwithstanding the fact that the spurious component B has a much greater effect upon the output signal than the desired component A.

Figure 3:
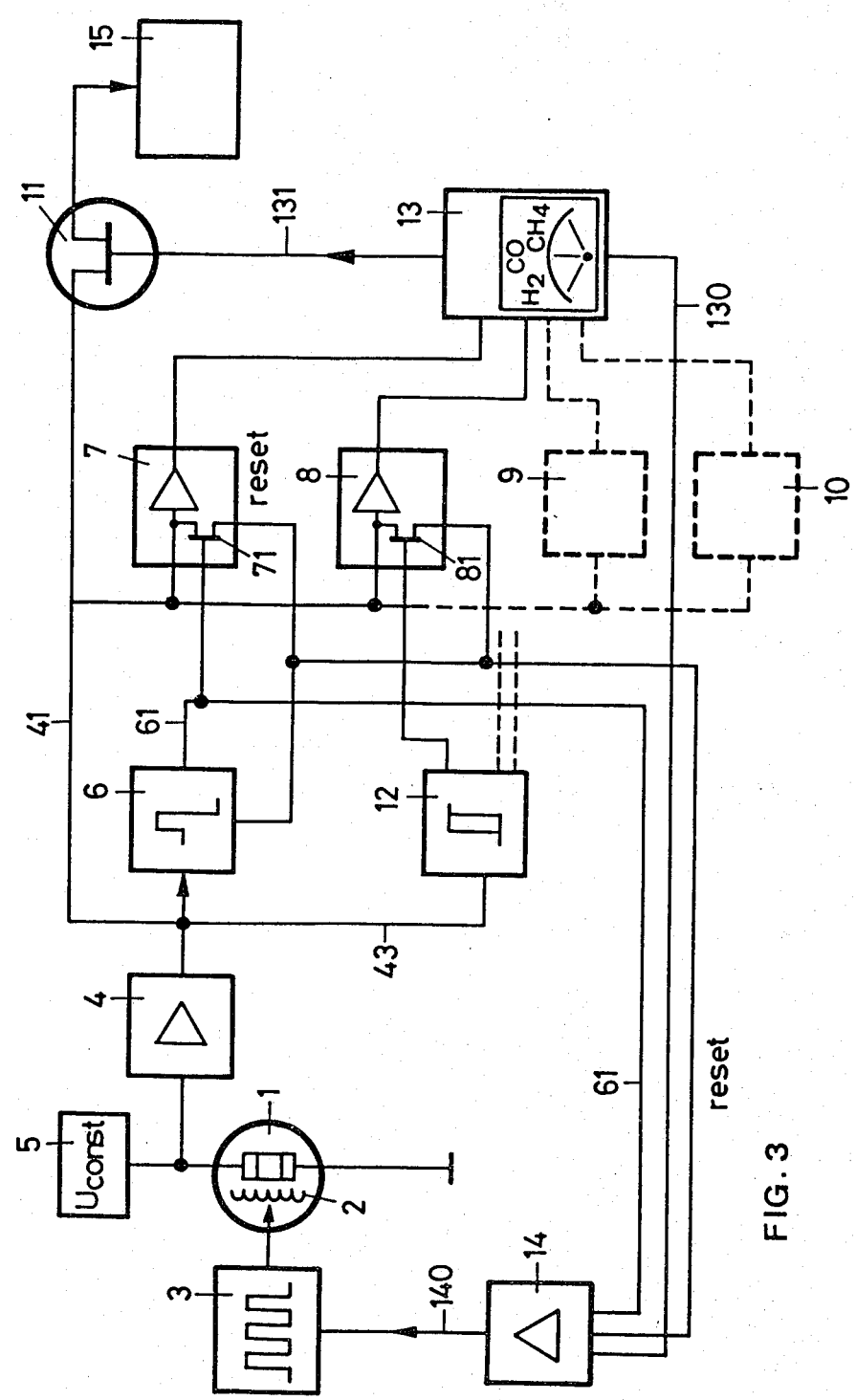
FIG. 3 illustrates an exemplary embodiment of an electronic circuit for evaluation of the output signal of the metal-oxide semiconductor.

In the description to follow there now will be explained the invention in conjunction with the second example discussed previously at the introductory portion of this disclosure. In the subterranean rooms of communication installations, such as central communication stations, repeater stations and cable chutes, it is possible for explosion-prone gases to penetrate the surroundings from the gas supply network. These should be removed. These gases have been illustrated in FIG. 1 by the component B. The hydrogen gas has been illustrated in FIG. 1 by the component A. The metal-oxide semiconductor, as already explained in conjunction with the first example, in this case is also set to the temperature $T_S$. In the presence of one or both components A and B the metal-oxide semiconductor possesses a conductivity $S_T$ and produces a corresponding output signal. In this case the electronic circuit, described in greater detail hereinafter in conjunction with FIG. 3, causes an increase of the temperature T by the amount $+\Delta T$. In this case for the desired gas or gas component B there results an increase in the output signal by the amount $\Delta SB_4$. For the non-desired gas or gas component A and which is to be considered as the spurious magnitude there results a reduction in the output signal by the amount $\Delta SA_3$. With this information the electronic circuit of FIG. 3 is capable of initiating the gas-specific defensive or protective measures.

Under the expression "gas-specific defensive or protective measures", or equivalent terminology, it is to be understood that, for instance, in order to eliminate the carbon monoxide (CO) there is turned-on the air circulation and venting system and for the elimination of the gasoline vapors, apart from accomplishing the air circulation and venting, there is additionally determined the source of the fault. If necessary, there then must be resorted to suitable measures in order to preclude any further outflow of gasoline. For instance, in the example of the communications installation, the gas-specific defensive protective measure is only related to the gases which flow out of the gas supply network into the surroundings.

Figure 2A:
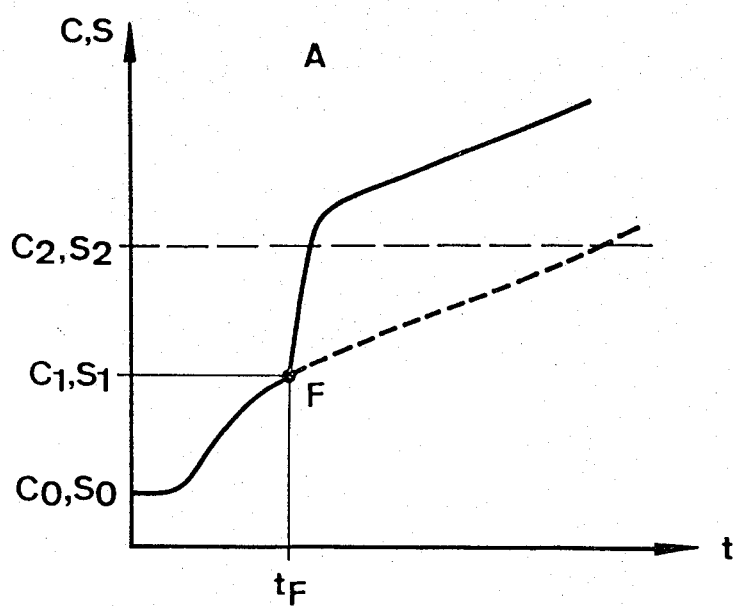
FIGS. 2a and 2b illustrate the timewise course of an output signal of a metal-oxide semiconductor upon the detection of a gas or vapor.
Figure 2B:
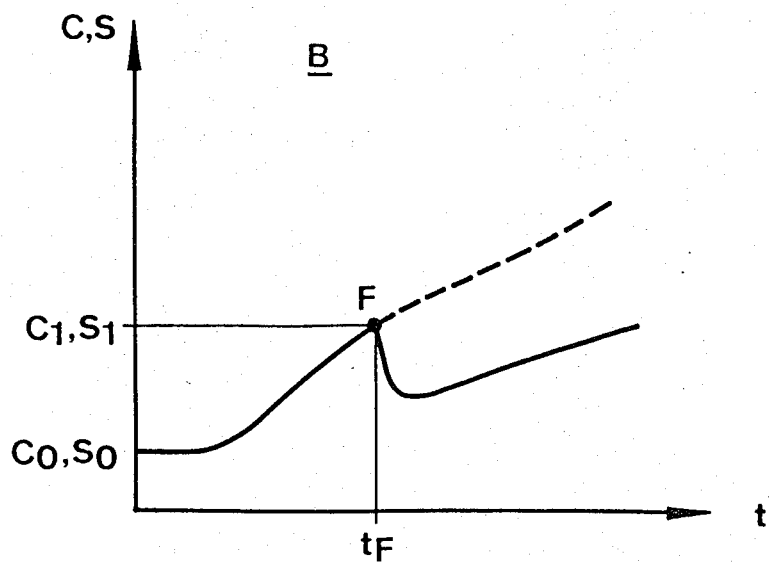

FIGS. 2a and 2b illustrate the timewise course of the change in the concentrations of the gases to be monitored and the conductivity of the metal-oxide semiconductor. FIG. 2a illustrates the relationships of the gas component A. The relationships for the gas component B have been illustrated in FIG. 2b. Along the abscissa of both FIGS. 2a and 2b there have been plotted time t. Along the ordinate of both FIGS. 2a and 2b there have been plotted the concentrations C of the gases or vapors, as the case may be, and the conductivity S of the metal-oxide semiconductor. It is now assumed that the gas component A according to FIG. 2a should be present with a concentration $C_0$ in the ambient air of the rooms which are to be monitored. The metal-oxide semiconductor has a conductivity $S_0$. The concentration of the gas component A now should increase throughout a certain time span. Upon reaching a threshold value of the concentration $C_1$ and the conductivity $S_1$, at the time $t_F$, the metal-oxide semiconductor delivers an output signal to the electronic circuit of FIG. 3. In FIG. 2a this point has been designated by reference character F. Now if, as already explained previously in conjunction with FIG. 1, the temperature of the metal-oxide semiconductor rapidly reduces by the amount $-\Delta T$, then the sensitivity of the metal-oxide semiconductor increases with respect to the gas component A, i.e. its conductivity is increased to $S_2$, so that the output signal at the electronic circuit likewise increases and, if needed, there can be signalled an alarm condition. In FIG. 2a there has been shown with broken lines from point F the increase of the concentration of the dangerous gas component A caused by an assumed gas intrusion. After an appreciably longer time it attains the concentration $C_2$ at which the conductivity, with constant temperature, reaches the value $S_2$ at which defensive measures must be initiated.

FIG. 2b shows the timewise course of the detection of the gas component B. This component B should be present at the concentration $C_0$ in the ambient air of the rooms to be monitored and should increase during the course of time to the value $C_1$. When there has been reached the concentration value $C_1$ at the time $t_F$, then the metal-oxide semiconductor possesses a conductivity $S_1$. The output signal, which now is inputted to the electronic circuit of FIG. 3, causes the temperature of the metal-oxide semiconductor to rapidly drop by the amount $-\Delta T$. Now if according to the illustration of FIG. 2b there is only present the gas component B in the surrounding air, then there results a reduction in the conductivity. The broken line of the curve shows the increase of the conductivity of the semiconductor owing to the increase in the concentration in the gas component B.

In FIG. 3 there has been illustrated an exemplary embodiment of electronic circuit for evaluation of the output signals of the metal-oxide semiconductor. The semiconductor 1 has spatial dimensions in the order of magnitude of 5×5 mm and is brought to the desired temperature by an electrical heater 2. The voltage of 0.1 to 10 volts for the heating wire of the electrical heater 2 is produced by a suitable heating voltage generator 3. This generator 3 adjusts the desired value of the voltage or potential. The temperature of the metal-oxide semiconductor 1 is set or adjusted in the manner already previously discussed in conjunction with FIGS. 1 and 2a and 2b. The metal-oxide semiconductor 1 is arranged in a room which has not been particularly illustrated in FIG. 3. It is assumed that the concentration of a gas, which for instance can be the component A, increases. The metal-oxide semiconductor 1 alters its conductivity S in corresponding fashion, as such has been depicted by FIGS. 1 and 2a. The voltage source 5 applies a constant potential to the metal-oxide semiconductor 1, whose voltage signals can be correspondingly amplified in an analog value-amplifier 4. The amplified voltage signals are inputted by means of a conductor or line 41 to a field-effect transistor 11 (FET) and to the response or switching circuits 7, 8, 9, 10 for the first, second, third and fourth peak values of the conductivity or, respectively, the concentration of the gas or the vapor. The same signals arrive by means of the line 43 at a threshold value switch 12 which, however, only generates one output signal when there have been obtained the conductivity threshold value after the temperature drop or temperature increases, as the case may be. In a comparator 6 the voltage signal, which provides information concerning the momentary conductivity of the semiconductor 1, is compared with set or reference values stored at that location, and which are present in conformity with the data available from the curves of FIG. 1. As long as at the temperature $T_S$ of the semiconductor 1 the concentration of the gas or vapor composed of a number of components has not reached the value $C_1$, the comparator 6 does not produce any output signal. In this case the conductivity value $S_1$ of FIGS. 2a and 2b has not been reached.

In order to explain the electronic circuit of FIG. 3, it is assumed that there has been reached the values $C_1$ and $S_1$. The comparator 6 now delivers an output signal to the line 61 which switches into its conductive state the FET 71 of the response circuit 7 for the first peak value. The same output signal arrives at the current circuit 14 which influences the heating voltage generator 3 by means of the line or conductor 140 in a manner such that the temperature of the metal-oxide semiconductor 1 increases or decreases (magnitude) in a suitable manner. The circuit 7 now causes the analog value-comparator 13 to input by means of the line 130 a signal to the current circuit 14, which by means of the line 140 influences the heating voltage generator 3 such that the heating voltage is altered in the desired direction (sign). In the exemplary embodiment under discussion the analog value-comparator 13 is programmed for hydrogen ($H_2$), carbon monoxide (CO) and methane ($CH_4$). Of course, programming it for other gases and/or vapors is readily possible. Now there is accomplished a temperature change in the desired directed (sign) by the amount $\Delta T$. This has already been more fully explained in conjunction with FIGS. 1, 2a and 2b. The change in the conductivity in the metal-oxide semiconductor 1, caused by the temperature changes, are perceived by changes in its output signal. It is now assumed that a reduction of the temperature by the value $-\Delta T$ has been undertaken, so that the voltage signal experiences an increase by the value $\Delta SA_1$ (FIG. 1). This voltage increase appears at the comparator 6 as well as by means of the line 41 at the response circuit 8 for the second peak value and by means of the line 43 at the threshold value switch 12 which now renders conductive or switches-through the FET 81 of the circuit 8. The circuit 8 now delivers to the analog value-comparator 13 the signal for the second peak values which detects the gas component A FIG. 1). Now if for this gas component A there are required specific protective or defensive measures, then such is programmed. The analog value-comparator 13, in this case, controls the FET 11 by means of the line 131 so as to assume its conductive state. The protective or defensive measures can now be initiated by the arrangement 15. Belonging to such protective or defensive measures are, for instance, acoustical or optical alarm units, air circulation devices, venting devices, extinguishing devices or the like. After the conductivity of the metal-oxide semiconductor 1 has dropped by reducing the concentration of the gas component A, then by means of the reset lines there is set the temperature of the metal-oxide semiconductor 1 to the original value $T_S$ (FIG. 1).

However, if only the gas component B (FIG. 1) is of significance, then in the circuit of FIG. 3 the analog value-comparator 13 is changed such that by means of the line 130 the current circuit 14 is caused to increase the heating voltage, so that the temperature of the metal-oxide semiconductor 1 increases by the value $+\Delta T$. The threshold value switch 15 and the circuit 8 need not be changed for this purpose. The electronic circuitry of FIG. 3 operates in the same manner as for the previously described lowering of the temperature of the value $-\Delta T$.

Now if the gas component B should be detected and the concentration of the closely thereat situated gas component A should increase up to the value S of the conductivity (FIG. 1), then the circuit 7 for the first peak value (FIG. 3), as already described, delivers a signal to the analog value-comparator 13. By means of the current circuit 14 the analog value-comparator 13 causes a temperature reduction which inputs the signal of the second peak value $\Delta SA_1$ and the signal of the reduction $\Delta SB_2$ by means of the line 41 to the circuit 8. The analog value-comparator 13 now has been informed that the gas component B is not present and therefore does not turn-on the alarm and the protective measures.

In the electronic circuitry of FIG. 3 there have been shown with broken lines further circuits 9 and 10 which are provided for the third and fourth peak values and so forth of the conductivity of the metal-oxide semiconductor 1. The circuits are placed into operation by the threshold value switch 12 which is programmed to the different peak values.

While there are shown and described present preferred embodiments of the invention, it is to be distinctly understood that the invention is not limited thereto, but may be otherwise variously embodied and practiced within the scope of the following claims. Accordingly,

What we claim is:

1. A method of reducing false alarms in gas warning installations caused by spurious gases and using as a gas-sensitive element a metal-oxide semiconductor operated at an essentially constant temperature, comprising the steps of:
    generating an output signal at the gas-sensitive element which is caused by the presence of an unknown gas or vapor composition;
    said output signal being predicated upon a change in the conductivity of the gas-sensitive element;
    rapidly changing the temperature of the gas-sensitive element in the presence of said output signal; and
    inputting the sign as well as the magnitude of the thus caused additional change in the output signal to an electronic circuit for discriminating the spurious gas.

2. A method for determining the composition of a gas mixture by means of a gas-sensitive element constructed as a metal-oxide semiconductor, and which gas-sensitive element is heated to an essentially constant temperature, comprising the steps of:
    in the presence of an output signal of the gas-sensitive element rapidly altering the temperature of the gas-sensitive element towards a positive or negative side to produce a signal change;
    superimposing the thus caused signal change as a function of magnitude and sign upon the output signal; and
    inputting the composite signal to an electronic circuit.

3. An apparatus for reducing false alarms in gas warning installations caused by spurious gases, comprising:
    a gas-sensitive element constituted by a metal-oxide semiconductor;
    a comparator for receiving a first output signal delivered by the gas-sensitive element;
    a circuit for a first peak value which is turned-on by the output signal of the gas-sensitive element; and
    an analog value-comparator which accomplishes a programmable change in the temperature of the metal-oxide semiconductor for discriminating the spurious gas.

4. The apparatus as defined in claim 3, further including:
    a threshold value switch for receiving a second and subsequent output signals of the gas-sensitive element constituted by the metal-oxide semiconductor;
    said threshold value switch preparing circuit correlated to the output signal for the second and following peak value of the electrical conductivity of the metal-oxide semiconductor; and the same output signal setting only the prepared switching circuit by means of a line.

5. An apparatus for determining the composition of a gas mixture by means of a gas-sensitive element constructed as a metal-oxide semiconductor, comprising:
- a gas-sensitive element constituted by a metal-oxide semiconductor;
- a comparator;
- a switching circuit operatively connected to said comparator;
- said comparator switching-on said switching circuit in the presence of a first peak value;
- an analog-value comparator connected in circuit with said switching circuit;
- said switching circuit causing said analog value-comparator to change the temperature of the metal-oxide semiconductor towards the positive or negative side by an amount $\Delta T$; and
- a threshold value switch for inputting a signal change to the analog value-comparator for analysis of the components of the gas or vapor.

6. The apparatus as defined in claim 5, further including:
- heating means for the metal-oxide semiconductor;
- a current circuit operatively connected with said heating means; and
- said analog value-comparator controlling by means of said current circuit said heating means of the metal-oxide semiconductor such that the temperature can be continuously changed over a sensitivity range of the semiconductor.

7. The apparatus as defined in claim 5, wherein:
- said threshold value switch receives a second and subsequent output signals of the gas-sensitive element constituted by the metal-oxide semiconductor;
- said threshold value switch preparing circuits correlated to the output signal for the second and following peak value of the electrical conductivity of the metal-oxide semiconductor; and
- the same output signals setting only the prepared switching circuit by means of a line.

* * * * *